United States Patent [19]

Weete et al.

[11] Patent Number: 4,943,389
[45] Date of Patent: Jul. 24, 1990

[54] EMULSIFIER FOR WATER-IN-OIL EMULSIONS

[75] Inventors: John D. Weete, Opelika, Ala.; George L. Griffith, Bethlehem, Pa.

[73] Assignee: Emulsion Technology, Inc., Parrish, Ala.

[21] Appl. No.: 177,956

[22] Filed: Apr. 4, 1988

[51] Int. Cl.$^5$ .............................................. B01F 17/14
[52] U.S. Cl. .................................. 252/308; 252/314; 252/356; 426/662
[58] Field of Search ................ 426/662; 252/308, 314, 252/356; 260/403

[56] References Cited

U.S. PATENT DOCUMENTS

| | | | |
|---|---|---|---|
| 2,223,558 | 3/1938 | Epstein | 252/308 |
| 2,552,706 | 3/1946 | Bertram | 252/314 X |
| 2,577,218 | 12/1947 | Waarden | 252/314 |
| 2,907,777 | 10/1959 | Cole | 260/403 |
| 3,026,341 | 3/1962 | Davis | 260/403 |
| 3,248,230 | 4/1966 | Houben et al. | 252/308 X |
| 3,318,704 | 5/1967 | Eichberg | 252/308 X |
| 3,505,074 | 4/1970 | Pardun | 260/403 |
| 3,962,292 | 6/1976 | Szuhaj et al. | 260/403 |
| 4,330,422 | 5/1982 | Tesch | 252/308 X |
| 4,400,295 | 8/1983 | Ootsu et al. | 252/356 |

FOREIGN PATENT DOCUMENTS

| | | | |
|---|---|---|---|
| 54-107530 | 8/1979 | Japan | 260/403 |
| 54-112825 | 9/1979 | Japan | 260/403 |
| 54-124009 | 9/1979 | Japan | 426/662 |
| 59-157193 | 9/1984 | Japan | 260/403 |

Primary Examiner—Matthew A. Thexton
Assistant Examiner—Daniel S. Metzmaier
Attorney, Agent, or Firm—Burns, Doane, Swecker & Mathis

[57] ABSTRACT

A unique and improved emulsifier for water-in-oil emulsions is provided by heating lecithin for a period of time sufficient to alter its composition such that the improved emulsifier is obtained. For example, the lecithin can be heated at a temperature in the range of from about 100° C. to about 250° C. for a period of time ranging from about 15 to about 480 minutes. The resultant thermally altered lecithin exhibits improved emulsification characteristics for water-in-oil emulsions. A water-in-oil emulsion comprised of a continuous oil phase, a discontinuous aqueous phase and the thermally altered lecithin exhibits excellent stability and an improved holding capacity with respect to the discontinuous aqueous phase.

25 Claims, No Drawings

EMULSIFIER FOR WATER-IN-OIL EMULSIONS

BACKGROUND OF THE INVENTION

1. Field of the Invention

The present invention relates to emulsifiers for use in water-in-oil emulsions. More particularly, the present invention relates to the use of thermally altered lecithin as an emulsifier for water-in-oil emulsions and the stable water-in-oil emulsions prepared therewith.

2. Description of the Prior Art

An emulsion can be defined as a dispersion of one immiscible liquid in another, stabilized by a third component, the emulsifying agent. Emulsion systems, however, by their very nature are thermodynamically unstable. See, for example, *Encyclopedia of Emulsion Technology*, Vol. 2, pp. 159–170. This inherent problem of stability has often resulted in limited applications for many potentially useful emulsion systems. Stable, improved emulsion systems exhibiting good holding capacities are therefore ever in demand and on the forefront of development.

Lecithin is well known, particularly as a surfactant and/or as an emulsifier. Lecithin is obtained from natural sources such as egg yolk, and plants such as soybean, maize, rapeseed, and the like where it is a by-product of vegetable oil refinement. The composition of commercial lecithin depends on the source, methods of preparation, and degree of purification, but in the most pure form it is comprised of mainly phosphatides. For example, granular soybean lecithin may contain principally phosphatidylcholine, phosphatidylethanolamine, phosphatidylinositol and the like.

The literature is replete with references to the use of lecithin in various applications. For example, the applications include the use of lecithin in:

- foodstuffs such as mayonnaise, sponge cake, confectioneries such as whipping cream and chocolate, dried dairy products such as powdered creams for coffee, and steam cooked noodles;
- cosmetics such as skin creams, shampoos and hair dressing agents;
- emulsions for producing doughs or batter for bakery products;
- pharmaceutical preparations, including acne preparations, antihemolytic emulsions, compositions for the treatment of bloat in ruminants, and carcinostatic drug compositions;
- non-stick cooking compositions used for coating cookware;
- vehicles for hard and soft gelatin capsules;
- polymer compositions, including polyester molding compositions, water soluble polyvinyl acetate films and a resin dispersion of an electrophotographer, as well as an asphalt emulsion for use in pavements;
- fungicide and pesticide dispersions;
- hydraulic fluids; and,
- emulsion explosive compositions.

While lecithin is well-known as an emulsifier, it has been recognized as a somewhat inferior emulsifier, particularly for water-in-oil emulsions. The use of lecithin as an emulsifier is therefore generally most preferred in oil-in-water type emulsions, or with the lecithin, due to its being an inexpensive source, filling the role as a secondary emulsifier in the presence of a primary emulsifier.

For example, the use of lecithin in emulsion explosives, wherein water-in-oil emulsions are often used, is well-documented. A number of publications exemplify this application. These include U.S. Pat. Nos. 4,602,970, 4,507,161, 4,473,418, 4,308,081, 4,357,184, 4,555,278, British Pat. Nos. 2,179,338 and 2,037,269; European Patent Application No. 0155800 and Australian Patent No. 10510/83. In all of these publications, the lecithin employed is used as an emulsifier or surfactant, with the lecithin being normal lecithin such as soybean lecithin. Some of these publications, however, do suggest that the lecithin should be used as a secondary emulsifier, and/or that lecithin is basically an inferior emulsifier.

The chemical modification of lecithin is known in the art as one manner in which to improve the lecithin for many different applications. U.S. Pat. No. 4,479,977, for example, discusses the acylation of lecithins to provide a clear, heat resistant lecithin useful as a release agent. Hydrolyzed lecithins are disclosed as being useful surfactants or emulsifiers. U.S. Pat. No. 4,547,387 discloses a rearrangement reaction product of a lecithin to form a better anti-spattering agent for margarine. Japanese Patent Application No. 61-162148 discloses a method for preparing a creamy emulsified oil or fat composition containing a milk component by adding a modified lecithin thereto. The modified lecithin is selected from a phosphatidylcholine-rich fractionated lecithin, a phosphatidylethanolamine- and/or phosphatidylinositol-rich fractionated lecithin, a partially hydrolyzed lecithin in which part of the fatty acids are hydrolytically removed, an acetylated lecithin, and a lecithin modified by a combination of fractionation, hydrolysis and acetylation. The chemical modification can vary greatly, therefore, depending on the ultimate application of the lecithin.

The heating of lecithin containing compositions, in general, is known. Such heating generally takes place in the form of a sterilization step or a drying step.

A few more specific instances of heating a lecithin containing composition include those described in U.S. Pat. No. 4,670,247 and U.S. Pat. No. 4,323,124. The first patent heats a composition containing lecithin to 180° C. for about one minute, and then at lower temperatures for more extended periods of time, in order to crosslink various major materials within the composition. The second patent, i.e., U.S. Pat. No. 4,323,124, injects lecithin with steam into a bore hole so that the lecithin acts as a coating for the rock formation. The injected steam is at a temperature of from 500 to 575° F.

In Japanese Patent Application No. 60-214845, there is disclosed the preparation of a powder for use as an emulsifier in the food industry, primarily for use by confectioners and noodle manufacturers. The method involves heating a mixture of lecithin and starch at a temperature of from the gelatinization temperature of the starch to 140° C. together with water to thereby form a lecithin-starch complex. This complex is then dried and powdered.

The problems encountered upon subjecting lecithin to heat are also recognized in the art, however, and solutions to avoid either using heat or to improve the chemical integrity of the lecithin at higher temperatures have been suggested.

For example, in U.S. Pat. No. 4,479,977, it is disclosed that the loss of chemical integrity by lecithin during heating is well documented. Lecithin is known to darken and give off odors upon heating. These changes are traced to a number of complex reactions between or within the phosphatide molecules. The object of the patent, therefore, is to avoid the decomposition of lecithin and improve its "chemical integrity" at higher temperatures. The solution suggested in the patent is acylating the lecithin in order to make it a heat resistant release agent.

U.S. Pat. No. 4,157,404 discloses a specific lecithin, i.e., yolk lecithin. The patent discloses that yolk lecithin is extremely susceptible to oxidation and therefore, when the yolk lecithin is heat treated at a temperature as high as 60° C. or more under atmospheric pressure, the color of yolk lecithin changes from yellowish orange to brown through yellowish brown. Accordingly, the patent suggests that a heat treatment to remove solvent in order to obtain a yolk lecithin is undesirable. The suggested route, in order to avoid the degradation of the yolk lecithin, is a novel solvent extraction method.

Thus, the two foregoing patents both discuss methods designed to avoid any heat treatment of lecithin. The suggestion is that upon heat treating lecithin, the results are bad and the resulting products are useless and/or undesirable.

While the use of lecithin in various applications is well known, including applications as an emulsifier, and various modifications of lecithin to improve its use in these applications have been suggested, a truly effective yet simple emulsifier based upon lecithin, particularly for water-in-oil emulsions, has heretofore been unknown to the art. The recognition and existence of such a simple, effective and easily obtained emulsifier would certainly benefit the industry and encourage the use of emulsion systems, and particularly water-in-oil emulsion systems.

Accordingly, it is an object of the present invention to provide a simple and easily prepared emulsifier composition which exhibits improved emulsification characteristics.

Yet another object of the present invention is to provide such an emulsifier composition which is particularly effective in stabilizing water-in-oil emulsions.

Still another object of the present invention is to provide a novel, stable water-in-oil emulsion which is comprised of such an emulsifier composition.

Another object of the present invention is to provide a simple, novel process for preparing a stable water-in-oil emulsion.

Yet another object of the present invention is to provide such a process for preparing a water-in-oil emulsion which exhibits good holding capacity with respect to the discontinuous aqueous phase.

These and other objects, as well as the scope, nature and utilization of the invention, will be apparent to those skilled in the art from the following description and the appended claims.

SUMMARY OF THE INVENTION

The foregoing objectives are realized by the present invention in providing a thermally altered lecithin composition which is useful for water-in-oil emulsions. Basically, the thermally altered lecithin is prepared simply by heating lecithin. This heating is generally conducted under conditions of temperature, time and pressure to sufficiently alter the composition, e.g., the acetone precipitable content and fatty acid content, such that the emulsification properties of the lecithin are improved. In a preferred embodiment, the lecithin is heated at a temperature in the range of from about 100° C. to about 250° C. for a period of time ranging from about 15 to about 480 minutes, for it has been found that upon thermally altering lecithin in this manner, a unique and improved emulsifier for water-in-oil emulsions is obtained.

Accordingly, in another preferred embodiment of the present invention, there is provided a water-in-oil emulsion comprised of
  (i) a continuous oil phase,
  (ii) a discontinuous aqueous phase, and
  (iii) an emulsion stabilizing amount of a thermally altered lecithin composition which has been prepared by heating lecithin at a temperature in the range of from about 100° C. to about 250° C. for a period of time ranging from about 15 to about 480 minutes. Such water-in-oil emulsions have been found to exhibit excellent stabilizing and holding capacity.

In another preferred embodiment of the present invention there is provided a process for preparing such a water-in-oil emulsion. The process can comprise the steps of
  (i) heating lecithin at a temperature in the range of from about 100° C. to about 250° C. for a period of time ranging from about 15 to about 480 minutes,
  (ii) mixing the product of (i) with an oil, and
  (iii) adding to the product of (ii) an aqueous phase with agitation to thereby yield a water-in-oil emulsion; or,
  (i) heating lecithin in an oil at a temperature in the range of from about 100° C. to about 250° C. for a period of time ranging from about 15 to about 480 minutes, and
  (ii) adding to the product of (i) an aqueous phase with agitation to thereby yield a water-in-oil emulsion. These processes have been found to be simple yet effective in producing a stable water-in-oil emulsion.

DETAILED DESCRIPTION OF THE PREFERRED EMBODIMENTS

The thermally altered lecithin composition of the present invention which is useful as an emulsifier for water-in-oil emulsions is prepared by heating lecithin (unaltered) in either the granular or fluid form. The heating is preferably conducted at a temperature in the range of from about 100° C. to about 250° C., more preferably at a temperature in the range of from about 160° C. to about 200° C., and most preferably at a temperature in the range of from about 175° C. to about 185° C. The duration of the heating is preferably for a length of time ranging from about 15 to about 480 minutes, and most preferably from about 60 to about 120 minutes. It has been found that such a heat treatment results in thermally induced chemical modifications of the lecithin, which manifest themselves in the acetone precipitable content and fatty acid content of the thermally altered lecithin, to provide a composition with significantly improved emulsification qualities.

In an alternative embodiment, the heating of the lecithin can be conducted in an oil which is to be used as the continuous phase in a water-in-oil emulsion. Such a heat treatment has also been found to result in a thermally altered lecithin composition exhibiting the unique and beneficial emulsification properties of the present invention, while essentially eliminating a step in the preparation of the water-in-oil emulsion. The heating of lecithin in oil is preferably conducted at the same temperature and for the same time periods noted previously with respect to the direct heating of lecithin.

It should also be noted that the preferred ranges of time and temperature noted previously may change somewhat based upon the pressure employed in the heating environment. The foregoing ranges are contemplated for use at atmospheric pressure. As the pressure changes, so may the temperature and time requirements of the heating step. The necessary changes, however, should become readily apparent to the skilled artisan.

The lecithin which can be used in the present invention can be lecithin derived from any plant, animal or microbial source. Suitable lecithin starting materials are commercially available, and include available soybean lecithin and yolk lecithin products. Lecithin derived from soybeans is most preferred. Examples of two soybean lecithin products that can be used successfully in the practice of this invention are CENTROLEXP (oil free phosphatides) granular lecithin (available from Central Soya Co., Inc., Fort Wayne, Ind. USA) and LECITHIN PRACTICAL (available from Eastman Kodak Co., Rochester, N.Y. USA). Another commercial lecithin source is Ross and Rowe, Inc., of Decatur, Ill.

Once the thermally altered lecithin has been prepared, a stable water-in-oil emulsion can be prepared using the thermally altered lecithin as the emulsifier. Such water-in-oil emulsions can be prepared by conventional means with the thermally altered lecithin being used as he emulsifier. However, a preferred process useful in the preparation of a water-in-oil emulsions in accordance with the present invention comprises the steps of
  (i) heating lecithin at a temperature in the range of from about 100° C. to about 250° C. for a period of time ranging from about 15 to about 480 minutes,
  (ii) mixing the product of (i) with an oil, and
  (iii) adding to the product of (ii) an aqueous phase with agitation to thereby yield a water-in-oil emulsion.

Alternatively, a preferred process useful in preparing the water-in-oil emulsion of the present invention can comprise the steps of
  (i) heating lecithin in an oil at a temperature in the range of from about 100° C. to about 250° C. for a period of time ranging from about 15 to about 480 minutes, and
  (ii) adding to the product of (i) an aqueous phase with agitation to thereby yield a water-in-oil emulsion. In a most preferred embodiment with respect to the latter process, the product of step (i) is allowed to cool to a temperature below 100° C. before the aqueous phase is added thereto, e.g., to preferably about 80° C.

In preparing the water-in-oil emulsions of the present invention, the oil of the continuous phase can be any suitable oil such as a vegetable oil or a mineral oil, or mixtures thereof. Among the preferred vegetable oils is soybean, sesame, safflower and cottonseed oils. Liquid paraffin is an example of a preferred mineral oil.

The discontinuous aqueous phase may consist of any dilute or concentrated aqueous solution involving a wide variety of organic or inorganic solutes, or a mixture of such substances. The final decision as to the content of the aqueous phase would depend, of course, on the intended application of the ultimate emulsion product.

It is preferred that the oil content of the water-in-oil emulsion ranges from about 1.5 to about 6.0 weight percent, and most preferably from about 1.8 to about 5.5 weight percent, based upon the weight of the total emulsion composition. The amount of thermally altered lecithin employed as the sole or primary emulsifier preferably range from about 0.05 to about 2.5 weight percent, and most preferably from about 0.08 to about 2.2 weight percent. The discontinuous phase may comprise any percentage of the total emulsion composition. However, for best results, subject, of course, to the intended application of the emulsion product, the content of discontinuous phase should be just below the maximum discontinuous phase holding capacity of the emulsifier/oil.

The resultant water-in-oil emulsions of the present invention exhibit excellent stability and holding capacity. In essence, the emulsions prepared with thermally altered lecithin in accordance with the present invention can hold as much as 183% more aqueous solution in the discontinuous phase than emulsions containing unaltered lecithin. Furthermore, such emulsions are stable for weeks compared to those prepared with unaltered lecithin, which show complete or partial deterioration within 24 hours.

In theory, it is believed that the thermalization of the lecithin brings about a series of chemical reactions that result in the optimization of the quality and quantity of specific lipophilic substances in a complex mixture such that, under the conditions favorable for emulsification, the organization of molecules into thermodynamically stable interfacial layers is maximized. As a result, extremely beneficial emulsification properties are exhibited in particularly, water-in-oil emulsions.

Among the compositional changes that have been observed a resulting from the chemical reactions brought about by the heating of lecithin for a period of time and at a temperature sufficient to improve the emulsification properties as described herein, are (1) a modest loss of weight (probably due mainly to the loss of water), (2) a substantial reduction in the amount of acetone precipitable substances which is characterized by the almost complete loss of non-choline containing phosphatides and reduction in the phosphatidylcholine content, i.e., phosphatidylcholine being essentially the only phosphatide remaining in the thermally altered lecithin preparation, and (3) a change in the phosphatidylcholine-fatty acid composition whereby the relative proportions of diunsaturated fatty acids are greatly reduced, the saturated fatty acids are substantially increased, and the triunsaturated fatty acid is absent. Among the characterizable new products formed during the thermalization of lecithin are triacylglycerols, free fatty acids and two types of condensable and esterifiable substances. Also observed is an uncharacterized dark brown substance(s) that is believed to be mainly a phosphatide reaction product(s).

The water-in-oil emulsions of the present invention prepared with thermally altered lecithin as described can be useful in a broad range of applications in areas where emulsions are currently employed, agriculture, pharmaceuticals, cosmetics, foods, etc. Applications in certain areas that heretofore have not envisioned a use for emulsions because of the lack of suitable emulsifiers that enable the preparation of sufficiently stable compositions with a broad range of properties might also be well served by the water-in-oil emulsions of the present invention.

The following examples are given as specific illustrations of the claimed invention and the benefits thereof. It should be understood, however, that the specific details set forth in the examples are merely illustrative and in nowise limitative. All parts and percentages in the example and the remainder of the specification are by weight unless otherwise specified.

In the examples, the following method was generally used in the preparation of an emulsion, unless otherwise specified:

The emulsifier was dissolved in oil and heated to a temperature of from 70° C. to 80° C. The discontinuous phase was heated to a similar temperature and poured slowly into the continuous phase while mixing vigorously with a kitchen food mixer. After all of the discontinuous phase had been added, the container of emulsion was removed from the heating apparatus and mixed further for 30 to 60 seconds. The continuous oil phase in the examples, unless otherwise noted, was an oil available under the trademark KLEAROL from Witco, Sonneborn Division, New York, N.Y. The discontinuous aqueous phase in the examples, unless otherwise noted, was a 40 percent sucrose solution.

The improved emulsification quality of thermally altered lecithin in accordance with the present invention as compared to unaltered lecithin was assessed in the examples by comparing two important properties of the respective emulsion products: (a) The discontinuous phase holding capacities (referred to hereafter as holding capacity) of the continuous phases containing the respective emulsifiers and (b) stability. Maintenance or changes in viscosity over time was also used as an indicator of stability or instability, respectively.

When the weight loss, acetone precipitable content, fatty acid content or phosphatide content was determined in the examples, the following methods were employed:

Weight loss—A known amount of lecithin was heated for a specified time and temperature, and the loss of weight was determined gravimetrically.

Acetone precipitable content—The amount of acetone precipitable material in the unaltered and thermally altered lecithin was determined by conventional methods, i.e., a small amount of a concentrated solution of lecithin was diluted with acetone. The insoluble material was collected by centrifugation, air-dried, and weighed.

The phosphatide and neutral lipid composition of the unaltered and thermally altered lecithin was determined by thin-layer chromatography as described in Weete, J. D., M. S. Sancholle, and C. Montant. (1983). Biochim. Biophys. Acta 752:19-29. The individual phosphatides were separated using chloroform: acetone: methanol:acetic acid:water (30:40:10:10:5 by vol.) as the developing solvent, and the neutral lipids were separated using hexane:diethyl ether:acetic acid (79:20:4 by vol.).

Fatty acid composition—The fatty acid composition of the phosphatidylcholine was determined by gas liquid chromatography as described in Weete, J. D., M. S. Sancholle, and C. Montant. (1983). Biochim. Biophys. Acta 752:19-29.

EXAMPLE 1

In Example 1, the viscosity and holding capacity of emulsions prepared with thermally altered lecithin in accordance with the present invention were measured. These emulsions demonstrate the outstanding attributes which characterize the emulsions of the present invention. Various emulsions comprised of thermally altered lecithin produced under different conditions of temperature and time were used. The measured viscosities and holding capacities, as well as the conditions of temperature and time used in preparing the thermally altered lecithin, are reported in Table 1 below.

TABLE 1

Properties of emulsions prepared with thermally altered lecithin produced under different conditions of temperature and time[a]

| Emulsion | Holding Capacity 40% sucrose (g) | Viscosity[b] (cps) |
|---|---|---|
| Time at 180° C. | | |
| 15 | 95 | 2000 |
| 30 | 113 | 2000 |
| 60 | 131 | 6000 |
| 90 | 143 | 11000 |
| 120 | 155 | 16000 |
| 240 | 149 | 12000 |
| 480 | 155 | 10000 |
| Temperature (°C.) for 60 minutes | | |
| 100 | 101 | 2000 |
| 125 | 101 | 2000 |
| 150 | 101 | 2000 |
| 175 | 131 | 4000 |
| 200 | 149 | 12000 |
| 225 | 167 | — |
| 250 | 179 | — |

[a]Emulsions were prepared using 0.3 g thermally altered lecithin and 5.7 g KLEAROL
[b]Viscosity measurements were made at 22-23° C. and at 20 RPM using a Brookfield Viscometer equipped with a #7 spindle.

Upon a review of the results, it can be seen that the holding capacity of the continuous phase prepared with thermally altered lecithin in accordance with the present invention as a function of time (30 to 480 minutes) at 180° C. increased from 95 to 143 grams up to 90 minutes of heating, and essentially leveled off at 155 grams for 120 to 480 minutes of heating. Overall, the holding capacity of the emulsion prepared with thermally altered lecithin as a function of time at constant temperature was increased by 63%.

The holding capacity of the continuous phase prepared with lecithin exposed to various temperatures (100 to 250° C.) for 60 minutes remained constant at 101 grams of discontinuous phase up to 175° C. and increased thereafter to 179 grams at 250° C. Overall, the holding capacity of emulsions prepared with thermally altered lecithin as a function of increasing temperature at constant time was increased by 78%.

EXAMPLE 2

To illustrate the significant improvement in the emulsification quality of lecithin through thermalization in accordance with the present invention, various emulsions were prepared with 6 grams of a continuous phase having different emulsifier/oil ratios using either thermally altered lecithin or unaltered lecithin. The holding capacities and viscosities of the emulsions were then measured. Table 2, below, reports the results.

TABLE 2

Comparison of emulsions prepared with thermally altered lecithin and unaltered lecithin as a function of emulsifier/oil ratio.[a,b]

| Emulsifier/oil ratio | Discontinuous phase Holding capacity (g) TL | Discontinuous phase Holding capacity (g) L | TL>L (%) | Viscosity (cps) TL | Viscosity (cps) L |
|---|---|---|---|---|---|
| 0.6/11.4 (TL and L) | 137 | 95 | 44 | 7000 | 2000 |
| 1.2/10.8 (TL) | 180 | — | 100 | 30000 | — |
| 1.25/10.75 (L) | — | 90 | | — | 4000 |
| 2.4/9.6 (TL) | 215 | — | 139 | 53000 | — |
| 2.5/9.5 (L) | — | 90 | | — | 6000 |

TABLE 2-continued

Comparison of emulsions prepared with thermally altered lecithin and unaltered lecithin as a function of emulsifier/oil ratio.[a,b]

| Emulsifier/oil ratio | Discontinuous phase Holding capacity (g) | | TL>L (%) | Viscosity (cps) | |
|---|---|---|---|---|---|
| | TL | L | | TL | L |
| 4.0/8.0 (TL) | 221 | — | — | — | — |
| 4.8/7.2 (TL) | 221 | — | 183 | 98000 | — |
| 4.5/7.5 (L) | — | 78 | | — | 6000 |

[a]TL = Thermally altered lecithin. TL emulsions were prepared with 6 g continuous phase and a 40% sucrose solution as the discontinuous phase. For viscosity measurements, emulsions were prepared as described except with 18 g less discontinuous phase than the holding capacity.
[b]L = Unaltered lecithin. L emulsions were prepared with 6 g continuous phase and a 40% sucrose solution as the discontinuous phase. For viscosity measurements, emulsions were prepared with 12 g less than holding capacity.

In Table 2, it can be seen that the holding capacities of emulsions prepared with unaltered lecithin were relatively constant with increasing emulsifier content in the continuous phase at 90 to 95 grams for emulsifier/oil ratios of 0.6/11.4, 1.25/10.75, and 2.5/9.5, and decreased to 78 grams for a ratio of 4.5/7.5. On the other hand, the holding capacities of emulsions prepared with thermally altered lecithin in accordance with the invention increased progressively with increasing emulsifier/oil ratio from 137 to 221 grams. The overall improvement of holding capacity with respect to emulsions prepared with unaltered lecithin was from 44% to 183%.

With respect to viscosity, the viscosities of emulsions prepared with 6 grams of continuous phase containing thermally altered lecithin, and a 40% sucrose solution as the discontinuous phase, increased progressively from 7000 cps at 0.6/11.4 to 98000 cps at 4.8/7.2, whereas the viscosities of corresponding emulsions prepared with unaltered lecithin increased only from 2000 cps to 6000 cps.

There was an overall 14-fold increase in viscosity over the emulsifier/oil ratio range tested for emulsions containing thermally altered lecithin as opposed to only a threefold increase for emulsions prepared with unaltered lecithin.

EXAMPLE 3

In Example 3, emulsions were prepared with 12 grams of thermally altered lecithin in approximately the same emulsifier/oil ratios as employed in Example 2, except that a 10% sucrose solution was used rather than a 40% solution as the discontinuous phase.

As can be seen from Table 3 below, increases in the holding capacity of the emulsions containing thermally altered lecithin vis-a-vis those containing unaltered lecithin were observed.

With respect to viscosity, the viscosities of the emulsions increased proportionately with increasing emulsifier/oil ratio, doubling with each doubling of the emulsifier content. The viscosity of emulsions prepared with unaltered lecithin increased 2.4 times at an emulsifier/oil ratio of 4.5/7.5 over that at 2.5/9.5. There was an overall 10.6-fold increase in emulsion viscosity over the emulsifier/oil ratio range tested. The range of viscosity values for the emulsions prepared with thermally altered lecithin was 10000 cps to 106000 cps (see Table 3). The viscosities of similarly prepared emulsions with unaltered lecithin as the emulsifier ranged only from 2000 cps to 14000 cps.

TABLE 3

Comparison of emulsions prepared with thermally altered lecithin and unaltered lecithin as a function of emulsifier/oil ratio[a]

| Emulsifier/oil ratio | Discontinuous Phase Holding Capacity (g) | | % Improvement (TL > L) | Visocosity (cps) | |
|---|---|---|---|---|---|
| | TL | L | | TL | L |
| 0.5/11.5 (TL) | 202 | — | 25 | 10000 | — |
| 0.6/11.4 (L) | — | 161 | | — | 2000 |
| 1.0/11.0 (TL) | 280 | — | 74 | 22000 | — |
| 1.25/10.75 (L) | — | 161 | | — | 3000 |
| 2.0/10 (TL) | 334 | — | 107 | 44000 | — |
| 2.5/9.5 (L) | — | 161 | | — | 5000 |
| 4.0/8.0 (TL) | 406 | — | 184 | 106000 | — |
| 4.5/7.5 (L) | — | 143 | | — | 14000 |
| 6.0/6.0 (TL) | 286 | — | — | — | — |

[a]Prepared using 12 g continuous phase and 10% sucrose as the discontinuous phase at 12 g less than holding capacity.

EXAMPLE 4

In this example, the holding capacity and viscosity of emulsions prepared in accordance with the present invention were monitored as a function of sucrose concentration in the discontinuous phase. The results are reported in Table 4 below.

From Table 4, it can be seen that the holding capacity of a continuous phase containing thermally altered lecithin increased as a function of solute concentration in the discontinuous phase. For example, the holding capacity increased 20% for emulsions with increasing sucrose concentration from 10% to 40%.

The viscosities of the emulsions prepared with thermally altered lecithin increased with increasing solute concentration of the discontinuous phase. For example, the viscosity of an emulsion prepared with a 10% sucrose solution was 4000 cps, and that prepared with 30% and 40% sucrose solutions was 6000 cps. While the emulsion prepared with the 10% sucrose solution became relatively unstable over extended periods of time and temperatures, the emulsion prepared with 30%, for example, remained relatively stable for more than 14-days with respect to viscosity at 4° C., room temperature, and 65° C.

TABLE 4

Properties of emulsions prepared with thermally altered lecithin as a function of sucrose concentration in the discontinuous phase.

| Sucrose concentration (%) | Discontinuous[a] Phase Holding Capacity (g) | Viscosity (cps)[b] | | | | | | |
|---|---|---|---|---|---|---|---|---|
| | | | 48 h | | | 336 h | | |
| | | 24 h | 4° C. | RT | 65° C. | 4° C. | RT | 65° C. |
| 10 | 119 | 4000 | B[c] | 4000 | B | B | 2000[d] | B |
| 20 | 113 | — | — | — | — | — | — | — |
| 30 | 137 | 6000 | 6000 | 5000 | 6000 | 4000 | 4000 | 6000[d] |

TABLE 4-continued

Properties of emulsions prepared with thermally altered lecithin as a function of sucrose concentration in the discontinuous phase.

| Sucrose concentration (%) | Discontinuous[a] Phase Holding Capacity (g) | Viscosity (cps)[b] | | | | | |
|---|---|---|---|---|---|---|---|
| | | | 48 h | | | 336 h | |
| | | 24 h | 4° C. | RT | 65° C. | 4° C. | RT | 65° C. |
| 40 | 143 | 6000 | — | — | — | — | — | — |

[a]Emulsions prepared with 6 grams (0.3 g/5.7 g) emulsifier/oil, otherwise emulsions were prepared with 12 grams (0.6 g/11.4 g) emulsifier oil and 173 grams discontinuous phase for the 10% sucrose solution and 185 grams discontinuous phase for the 30% and 40% sucrose solutions.
[b]Time of measurement after emulsion preparation
[c]B = Broken emulsion
[d]Water droplets appearing on surface.

EXAMPLE 5

In this example, lecithin was thermally altered in situ (while dissolved in oil) and the holding capacity of the continuous phase was determined as a function of lecithin originally placed into the oil prior to thermalization. Unaltered lecithin (1.25 g, 2.5 g, 3.75 g, and 5.0 g) was dissolved in 23.75 grams of oil and heated at 180° C. for 60 minutes. Corresponding solutions with unaltered lecithin were used for comparison. The results of the comparisons are reported in Table 5 below, from which it can be seen that the holding capacity of the continuous phases containing thermally altered lecithin in accordance with the present invention increase progressively over the corresponding phases containing unaltered lecithin as a function of increasing emulsifier concentration, the increase being from about 15% to 152%.

TABLE 5

Discontinuous phase holding capacities of continuous phases containing lecithin thermalized directly in oil, or unaltered lecithin.[a]

| Emulsifier (g/23.75 g oil) | Holding Capacity (g) | | TL > L (%) |
|---|---|---|---|
| | L[b] | TL | |
| 1.25 | 119 | 137 | 15 |
| 2.50 | 95 | 143 | 51 |
| 3.75 | 90 | 185 | 106 |
| 5.0 | 95 | 239 | 152 |

[a]Discontinuous phase was a 40% sucrose solution and 6 grams of continuous phase were used for emulsion preparation.
[b]Unstable emulsions.

EXAMPLE 6

In this example, emulsion stability was measured as resistance to phase separation with increasing centrifugal force at a constant time and upon standing with time and temperature. For the purpose of this illustration, phase separation refers to the non-random distribution of the particles (cells) containing the aqueous solution in the continuous phase, i.e., settling under the force of gravity. The emulsions are referred to as "broken" when the particles either coalesce forming larger particles or rupture whereby pockets of aqueous phase form within the emulsion and can be separated by centrifugation. In addition, a decrease in viscosity with time was also used as a measure of deterioration in stability. Stability as a function of pH was also determined.

The measured stabilities of various emulsions made from lecithin prepared as a function of temperature and time of exposure to 180° C. as measured by phase separation are given in Table 6 below. After 6-days of standing at 22–23° C., the emulsions prepared using thermally altered lecithin exhibited good stability.

Emulsions prepared with unaltered lecithin at various emulsifier/oil concentrations were generally unstable and exhibited complete or partial phase separation and breakdown within 24 hours of preparation. The best emulsion prepared with unaltered lecithin contained 4.5 grams emulsifier and 7.5 grams of oil. This creamy-yellow emulsion was stable for 48 hours but thereafter began to show phase separation and breakdown. Upon centrifugation of this emulsion at 2000 rpm for 10 minutes soon after preparation, some water settled to the bottom of the tube and oil rose to the top.

TABLE 6

Stability of emulsions prepared with thermally altered lecithin as function of emulsifier preparation temperature and time[a]

| Emulsifier Preparation Conditions | Stability | |
|---|---|---|
| | 24 hours | 144 hours |
| Time (minutes) at 180° C. | | |
| 15 | some oil separation | complete breakdown |
| 30 | some oil separation | considerable breakdown |
| 60 | good | good |
| 90 | good | good |
| 120 | good | good |
| 240 | good | good |
| 480 | some water droplets | some water droplets |
| Temperature (°C.) for 60 minutes | | |
| 100 | good | complete breakdown |
| 125 | good | considerable breakdown |
| 150 | some oil separation | considerable breakdown |
| 175 | good | good |
| 200 | good | good |
| 225 | complete breakdown | no emulsion |
| 250 | complete breakdown | no emulsion |

[a]Stability measured visually after standing at room temperature for specified periods, and was based on phase separation.

EXAMPLE 7

This example was directed to the effect of pH condition on the emulsions of the subject invention. Emulsions were prepared using 6 grams of thermally altered lecithin/oil (0.3/5.7) and a 40% sucrose solution adjusted to the desired pH (1 to 11) with either HCl or NaOH as the discontinuous phase. Various properties of the emulsions were then determined, which are reported in Table 7 below.

Good stable emulsions were formed with the discontinuous phase having pH values at 1 to 9. No emulsion was formed at pH 11. There was very little variation in the holding capacity of the emulsions as a function of pH in the 1 to 7 range, although a pH less than 5 was slightly more favorable in this regard. The emulsion prepared at pH 9 held 29% less discontinuous phase than that prepared at pH 7.

TABLE 7
Effects of pH on properties of emulsions prepared with thermally altered lecithin (TL)[a]

| Emulsion PH | Discontinuous Phase Holding Capacity (g) | Viscosity (cps) | Water loss[b] (mg) |
|---|---|---|---|
| 1 | 149 | — | — |
| 3 | 149 | 6000 | 344 |
| 5 | 143 | 6000 | 325 |
| 7 | 143 | 6000 | 358 |
| 9 | 101 | 6000 | 358 |
| 11 | No emulsion | — | — |

[a]Emulsions prepared with 6 g continuous phase (0.3 g TL and 5.7 g Klearol) and 40% (w/v) sucrose solution as the discontinuous phase. pH was adjusted with HCl or NaOH.
[b]Water loss in a desiccating environment for 20 hours.

EXAMPLE 8

Emulsions were prepared using varying amounts of continuous phase, discontinuous phase and emulsifier/oil ratios. Both thermally altered lecithin and unaltered lecithin were employed as emulsifiers, as indicated in Table 8 below. The viscosity and permeability of the various emulsions were determined. The results are reported in Table 8 below.

The term permeability in the context of the present illustration is used to indicate the loss of water from the emulsion as a function of time under desiccating conditions (a sealed container with $CaCl_2$ as the dessicant).

TABLE 8
Comparison of emulsions prepared with thermally alterd (TL) And unaltered lecithin (L)

| Emulsifier | Continuous Phase (g) | Emulsifier/Oil Ratio | Discontinuous Phase (g) | Viscosity (cps) | Permeability (mg) 48 h | Permeability (mg) 120 h |
|---|---|---|---|---|---|---|
| L | 36 | 0.6/11.4 | 286 | 2000 | 230 | 584 |
| TL | 36 | 0.6/11.4 | 286 | 3000 | 264 | 837 |
| L | 24 | 4.5/7.5 | 239 | 4000 | 622 | 958 |
| TL | 24 | 4.5/7.5 | 239 | 1100 | 511 | 972 |
| TL | 12 | 0.6/11.4 | 358 | 10000 | 594 | 1047 |
| TL | 12 | 4.5/7.5 | 358 | 89000 | 538 | 1035 |

EXAMPLE 9

Various emulsions were prepared using thermally altered lecithin in differing emulsifier/oil ratios. The viscosity and permeability of the resultant emulsions were then measured. The results are reported in Table 9 below.

TABLE 9
Comparison of emulsions prepared with thermally alterd lecithin as a function of emulsifier/oil ratio.[a]

| Emulsifier/Oil Ratio (g) | (Amount) (g) | Discontinuous Phase (g) | Viscosity[b] (cps) | Permeability (mg $H_2O$) 48 h | Permeability (mg $H_2O$) 72 h |
|---|---|---|---|---|---|
| GE1 0.6/11.4 | 24 | 358 | 6000 | 435 | 616 |
| GE2 1.5/10.5 | 12 | 263 | 17000 | 466 | 634 |
| GE3 3.0/9.0 | 12 | 334 | 39000 | 406 | 566 |
| GE4 4.5/7.5 | 12 | 358 | 86000 | 340 | 486 |

[a]Emulsions were prepared with a 40% sucrose solution as the discontinuous phase.
[b]Viscosities were recorded 24 hours after preparation.

EXAMPLE 10

The four emulsions prepared in Example 9 were tested for viscosity after being subjected to different temperatures. Viscosity measurements were made after 48 hours and after 14 days. The results are reported in Table 10 below. The results indicate that the emulsions remained remarkably stable with respect to viscosity for more than 14 days, regardless of temperature.

TABLE 10
Effects of temperatures on the viscosity of emulsions prepared with thermally altered lecithin.[d]

| Temperature (c) (°C.) | GE1 (a) | GE1 (b) | GE2 (a) | GE2 (b) | GE3 (a) | GE3 (b) | GE4 (a) | GE4 (b) |
|---|---|---|---|---|---|---|---|---|
| 4 | 6000 | 5000 | 17000 | 18000 | 40000 | 48000 | 81000 | 98000 |
| 22–23 | 6000 | 5000 | 17000 | 19000 | 37000 | 47000 | 89000 | 97000 |
| 65 | 6000 | 8000 | 17000 | 16000 | 39000 | 47000 | 62000 | 61000 |

(a) Measurement made 48 hours after emulsion preparation.
(b) Measurement made 336 hours (14 days) after emulsion preparation.
(c) Emulsions were placed at the respective temperatures within a few hours after preparation. After 24 hours, the emulsions were allowed to come to room temperature (22–23° C.) prior to taking viscosity measurements. The emulsions were left at room temperature thereafter during the 14 day measurement period.
(d) See Table 9 for GE emulsion designations

EXAMPLE 11

Various emulsions were prepared with 6 grams of a continuous phase containing 0.3 g thermally altered lecithin and 5.7 g Klearol, and a discontinuous phase containing either 5% or 15% glycine at pH values of 4, 7, and 9 for each concentration. The holding capacity, viscosity and water loss after 24 hours was then measured for each of the various emulsions. The results are reported in Table 11 below.

TABLE II

Properties of emulsions prepared with glycine as a component of the discontinuous phase[a]

| Discontinuous Phase | Discontinuous Phase Holding Capacity (g) | Viscosity (cp) | Water loss After 24 hours (mg) |
|---|---|---|---|
| Glycine (5%) | | | |
| pH 4 | 85 | 6000 | 45.6 |
| pH 7 | 80 | 8000 | 46.1 |
| pH 9 | 70 | No emulsion | — |
| Glycine (15%) | | | |
| pH 4 | 110 | 10,000 | 32.6 |
| pH 7 | 95 | 11,000 | 35.2 |
| pH 9 | 80 | 6,000 | 38.0 |

[a]Except for determining discontinuous phase holding capacity, the emulsions were prepared with 6 g (0.3 g TL/5.7 g Klearol) continuous phase and 75 ml of the discontinuous phase, except for glycine (5%) at pH 9 which held only 70 ml.

EXAMPLE 12

For the purpose of this example, an emulsion was prepared with thermally altered lecithin/oil (0.3 g/5.7 g) as the continuous phase and 10% NaCl as the discontinuous phase. The holding capacity of this continuous phase was 113 grams, and the viscosity of such an emulsion prepared with 101.4 grams of 10% NaCl solution was 13,000 cps.

The properties of emulsions prepared with thermally altered lecithin and discontinuous phases containing either 5%, 10% or 20% NaCl solutions were also observed. The holding capacity increased 45% over the NaCl concentration range, and the viscosity increased from 3000 to 14000 cps, or 4.7-fold. These results are reported in Table I2 below.

TABLE 12

Properties of emulsions prepared with thermally altered lecithin and sodium chloride as the solute of the discontinuous phase[a].

| NaCl (%) | Discontinuous Phase Holding Capacity (g) | Viscosity (cps) |
|---|---|---|
| 5 | 90 | 3000 |
| 10 | 119 | 11000 |
| 20 | 131 | 14000 |

[a]Emulsions were prepared with 6 grams of continuous phase (0.3/5.7, emulsifier/oil).

EXAMPLE 13

The weight loss of lecithin at 180° C. for various heating times was measured. Beginning with 25 grams of lecithin, 1.5 to 3.5% of the original weight of the lecithin was progressively lost during heating at 180° C. for 30 to 480 minutes. Most of the weight reduction would be expected to be due to the loss of water, but a small amount of the material would also be expected to be volatile organic substances produced during thermalization. The results are reported in Table 13 below.

TABLE 13

Weight loss during the thermalization of lecithin as a function of time.[a]

| Lecithin (g) | Heating Time (min.) | Loss Wt. (g) | Percentage of Wt. Loss |
|---|---|---|---|
| 25 | 15 | 0 | 0 |
| 25 | 30 | 0.37 | 1.5 |
| 25 | 60 | 0.52 | 2.1 |
| 25 | 90 | 0.63 | 2.5 |
| 25 | 120 | 0.68 | 2.7 |
| 25 | 240 | 0.87 | 3.5 |
| 25 | 480 | 0.93 | 3.7 |
| 100 | 90 | 2.60 | 2.6 |

[a]Thermalization at 180° C.

EXAMPLE 14

Various lecithin samples were heated for 60 minutes at a selected temperature. The change in acetone precipitable content was then measured, with the results being reported in Table 14 below.

TABLE 14

Acetone precipitable contents of lecithin as a function of thermalization temperature.[a]

| Temperature (°C.) | Sample Weight | Acetone Precipitate | Percent of Total |
|---|---|---|---|
| 100 | 229.5 | 219.3 | 95.6 |
| 125 | 219.8 | 178.9 | 81.3 |
| 150 | 236.0 | 147.4 | 62.5 |
| 175 | 196.5 | 80.3 | 40.9 |
| 200 | 282.5 | 86.3 | 30.6 |
| 225 | 263.3 | 90.4 | 34.4 |
| 250 | 295.2 | 100.9 | 34.2 |

[a]Heated for 60 minutes at the respective temperatures.

Acetone precipitable substances (phosphatides) comprised about 95% percent of the granular lecithin (Centrolex P, Central Soya, Decatur, Ind.) used. Thermalization up to 200° C. resulted in a 68% reduction in acetone precipitable substances, and the content of these substances remained relatively constant at 31 to 34% of the total weight of the thermally altered lecithin thereafter up to 250° C. Between 30 and 60 minutes were required to achieve maximum reduction of the acetone precipitable substances when the lecithin was heated at 180° C., and the content of these substances remained relatively constant thereafter up to 480 minutes exposure to this temperature.

EXAMPLE 15

Various samples of lecithin were heated at 180° C. for differing lengths of time. The acetone precipitable contents of the heated sample was then measured. The results are reported in Table 15 below.

TABLE 15

Acetone precipitable contents of lecithin as a function of thermalization time.[a]

| Time (min.) | Sample Weight (mg) | Acetone Precipitate (mg) | Percent (%) |
|---|---|---|---|
| 15 | 199.6 | 183.2 | 91.8 |
| 30 | 203.6 | 143.6 | 70.5 |
| 60 | 202.0 | 64.5 | 31.9 |
| 90 | 390.4 | 112.5 | 28.8 |
| 120 | 299.9 | 90.7 | 30.2 |
| 240 | 217.9 | 60.1 | 27.6 |
| 480 | 350.2 | 108.2 | 30.9 |

[a]Heated at 180° C. for respective times.

All of the phosphatides in the acetone precipitable fraction of the lecithin were reduced by thermalization as described in the Table above, but essentially all of the noncholine phosphatides were degraded and thus eliminated from the product. The phosphatidylcholine was also reduced considerably.

The neutral fraction of the thermally altered lecithin contained mainly triacylglycerols, free fatty acids, and two classes of substances unidentified.

EXAMPLE 16

The fatty acid composition of phosphatidylcholine isolated from thermally altered lecithin and unaltered lecithin was compared. It was found that there was an overall increase in the degree of saturation associated with the thermally altered product as shown by a doublin of the relative contents of palmitic and stearic acids, and to the elimination of the most unsaturated component of the phosphatidylcholine molecule, linolenic acid, and reduction by half of linoleic acid. These results are shown in Table 16 below.

TABLE 16

Fatty acid composition of phosphatidylcholine from lecithin before and after thermalization.[a]

| Fatty Acid | Relative Percent (%) | |
|---|---|---|
| | Unaltered Lecithin | Thermally Altered Lecithin |
| Palmitic | 21.3 | 42.2 |
| Stearic | 5.7 | 13.9 |
| Oleic | 8.0 | 17.2 |
| Linoleic | 58.5 | 26.6 |
| Linolenic | 6.5 | — |

[a]Thermalization for 90 min at 180° C.

EXAMPLE 17

An emulsion was prepared with a thermally altered lecithin/oil ratio of 3 g/5 g as the continuous phase, and 188.2 grams of an 80% ammonium nitrate solution containing 2 grams urea and 1.2 grams triethanolamine as the discontinuous phase. The objective of this example was to demonstrate that an aqueous solution of a very high salt concentration can be effectively emulsified using thermally altered lecithin as the emulsifier into a highly stable emulsion. The resulting emulsion was found very stable in that there was no phase separation and no crystallization of the ammonium nitrate within the supersaturated discontinuous phase for over three months after preparation. The emulsion prepared had a viscosity of 56,000 cps.

EXAMPLE 18

The rates of water loss from emulsions prepared with a continuous phase containing different thermally altered lecithin/oil ratios during the first 48 hours in the desiccating environment described in Example 8 was explored in this Example. It was found that the rate of water loss was essentially the same for emulsions with ratios of 0.6/11.4 and 1.2/10.75, but the rates decreased progressively with increasing thermally altered lecithin contents of 2.5/9.5 and 4.5/7.5. However, after 144 hours, the amount of water lost in the three emulsions having the lowest emulsifier/oil ratios was essentially the same, and it would be expected that after an additional 48 to 72 hours all of the above emulsions would have lost the same amount of water. Generally, water loss from the emulsion was inversely related to the concentration of the solution in the discontinuous phase.

EXAMPLE 19

A comparative emulsion was prepared with unaltered lecithin in an emulsifier/oil ratio of 4.5/7.5. The emulsion had a viscosity of 15,000 cps. The viscosity of this emulsion dropped with time at room temperature to 9,000 cps at 48 hours, 4,000 cps at 72 hours and 3,000 cps at 96 hours, which indicated a progressive deterioration with time.

EXAMPLE 20

Emulsions were prepared using a constant (0.3 g) amount of thermally altered lecithin and varying oil (Klearol) contents, and 40% sucrose as the discontinuous phase, to determine the effect of oil content on emulsion formation and the stability of such emulsions. The results are reported in Table 17 below.

The holding capacity of the continuous phases increased progressively with increasing oil content from 150 g at 6 g of oil to 360 g at 20 g of oil which is a 140% increase in holding capacity. The emulsion having the lowest oil content had the highest viscosity at 6000 cps, and that of the emulsion containing 9 g oil was 4000 cps. The viscosity of emulsions containing 12 to 20 g of oil was 2000 cps.

The emulsion containing only 6 g of oil lost the greatest amount of water 4 days after preparation but 2 days in the dessiccating environment, whereas water loss from the other emulsions was relatively constant. The emulsions containing 6 and 9 g of oil remained stable for at least 18 days after preparation, but the ones with higher oil contents showed phase separation after 6 days and had decomposed after 14 days.

TABLE 17

| Emulsion | Klearol (g) | % TL in Emulsion | % Klearol in Emulsion | Discontinuous[b] Phase Holding Capacity (g) | % Discontinuous Phase | Viscosity[c,d] (cps) | Water loss (mg) |
|---|---|---|---|---|---|---|---|
| KV1 | 6 | 0.19 | 3.8 | 150 | 96.0 | 6000 | 805 |
| KV2 | 9 | 0.15 | 4.8 | 180 | 95.0 | 4000 | 709 |
| KV3 | 12 | 0.13 | 5.4 | 210 | 94.5 | 2000 | 674 |
| KV4 | 15 | 0.10 | 5.1 | 276 | 94.8 | 2000 | 728 |
| KV5 | 20 | 0.08 | 5.3 | 360 | 94.7 | 2000 | 671 |

[a]Thermally altered lecithin content of each emulsion was 0.3 g.
[b]40% sucrose was the discontinuous phase used.
[c]Values given were taken 11 days after emulsion preparation. They remained stable during this period.
[d]Each emulsion was prepared at 18 g under the discontinuous phase holding capacity.

Although the invention has been described with preferred embodiments, it is to be understood that variations and modifications may be resorted to as will be apparent to those skilled in the art. Such variations and modifications are to be considered within the purview and the scope of the claims appended hereto.

What is claimed is:

1. A water-in-oil emulsion comprised of
(i) a continuous oil phase,
(ii) a discontinuous aqueous phase, and
(iii) an emulsion stabilizing amount of a thermally altered lecithin composition which has been prepare by heating lecithin at a temperature in the range of from about 100° C. to about 250° C. for a period of time ranging from about 15 to about 480 minutes.

2. The water-in-oil emulsion of claim 1, wherein the thermally altered lecithin has been prepared by heating at a temperature in the range of from about 160° C. to about 200° C.

3. The water-in-oil emulsion of claim 1, wherein the thermally altered lecithin has been prepared by heating at a temperature in the range of from about 175° C. to about 185° C.

4. The water-in-oil emulsion of claim 1, wherein the thermally altered lecithin has been prepared by heating for a period of time ranging from about 60 to about 480 minutes.

5. The water-in-oil emulsion of claim 1, wherein the thermally altered lecithin has been prepared by heating for a period of time ranging from about 60 to about 120 minutes.

6. The water-in-oil emulsion of claim 1, wherein the thermally altered lecithin has been prepared by heating at a temperature in the range of from about 160° C. to about 200° C. for a period of time ranging from about 60 to about 480 minutes.

7. The water-in-oil emulsion of claim 6, wherein the thermally altered lecithin has been prepared by heating at a temperature in the range of from bout 170° C. to about 185° C. for a period of time ranging from about 60 to about 120 minutes.

8. The water-in-oil emulsion of claim 1, wherein the continuous oil phase comprises from about 1.5 to about 6.0 percent by weight of the total emulsion composition.

9. The water-in-oil emulsion of claim 8, wherein the continuous oil phase comprises from about 1.8 to about 5.5 weight percent of the total emulsion composition.

10. The water-in-oil emulsion of claim 1, wherein the thermally altered lecithin composition comprises from about 0.05 to about 2.5 weight percent of the total emulsion composition.

11. The water-in-oil emulsion of claim 10, wherein the thermally altered lecithin composition comprises from about 0.08 to about 2.2 weight percent of the total emulsion composition.

12. The water-in-oil emulsion of claim 1, wherein the continuous oil phase comprises from about 1.8 to about 5.5 weight percent of the total emulsion composition, and the thermally altered lecithin composition comprises from about 0.08 to about 2.2 weight percent of the total emulsion composition.

13. The water-in-oil emulsion of claim 1, wherein the weight ratio of thermally altered lecithin composition to continuous oil phase ranges from about 0.5/11.5 to about 1.

14. The water-in-oil emulsion of claim 1, wherein the weight ratio of thermally altered lecithin composition to continuous oil phase ranges from about 0.6/11.4 to about 4.8/7.2.

15. The water-in-oil emulsion of claim 12, wherein the weight ratio of thermally altered lecithin composition to continuous oil phase ranges from about 0.6/11.4 to about 4.8/7.2.

16. The water-in-oil emulsion of claim 1, wherein the pH of the discontinuous aqueous phase ranges from about 1 to about 9.

17. The water-in-oil emulsion of claim 1, wherein the pH of the discontinuous aqueous phase ranges from about 1 to about 7.

18. The water-in-oil emulsion of claim 1, wherein the pH of the discontinuous aqueous phase ranges from about 1 to about 5.

19. The water-in-oil emulsion of claim 15, wherein the pH of the discontinuous aqueous phase ranges from about 1 to about 5.

20. The water-in-oil emulsion of claim 1, wherein the discontinuous aqueous phase is comprised of an amino acid, carbohydrate or salt.

21. The water-in-oil emulsion of claim 20, wherein the discontinuous aqueous phase is comprised of a salt.

22. The water-in-oil emulsion of claim 21, wherein the discontinuous aqueous phase is comprised of ammonium nitrate.

23. The water-in-oil emulsion of claim 20, wherein the discontinuous aqueous phase is comprised of glycine, sucrose, sodium chloride or ammonium nitrate.

24. The water-in-oil emulsion of claim 15, wherein the discontinuous aqueous phase is comprised of ammonium nitrate.

25. The water-in-oil emulsion of claim 1, wherein the thermally altered lecithin is prepared from soybean lecithin.

* * * * *